(12) United States Patent  
Hammond

(10) Patent No.: US 8,920,608 B2  
(45) Date of Patent: Dec. 30, 2014

(54) METHOD OF TREATING SLUDGE USING SOLAR ENERGY

(71) Applicant: Gary Hammond, Leesburg, FL (US)

(72) Inventor: Gary Hammond, Leesburg, FL (US)

( * ) Notice: Subject to any disclaimer, the term of this patent is extended or adjusted under 35 U.S.C. 154(b) by 13 days.

(21) Appl. No.: 13/900,606

(22) Filed: May 23, 2013

(65) Prior Publication Data

US 2014/0205497 A1  Jul. 24, 2014

Related U.S. Application Data

(63) Continuation-in-part of application No. 13/745,266, filed on Jan. 18, 2013.

(51) Int. Cl.  
*B01D 1/00* (2006.01)  
*A61L 2/04* (2006.01)

(52) U.S. Cl.  
CPC . *A61L 2/04* (2013.01); *Y10S 203/01* (2013.01)  
USPC ............ 203/86; 203/DIG. 1; 202/96; 202/99; 159/1.1; 159/47.1

(58) Field of Classification Search  
USPC ............. 203/86, DIG. 1; 202/96, 99; 159/1.1, 159/47.1, 903  
See application file for complete search history.

(56) References Cited

U.S. PATENT DOCUMENTS

| | | | |
|---|---|---|---|
| 8,070,835 B2* | 12/2011 | McAlister | 44/300 |
| 8,256,382 B2* | 9/2012 | Ba-abbad | 119/450 |
| 2011/0315539 A1* | 12/2011 | Zadik et al. | 202/99 |
| 2011/0315542 A1* | 12/2011 | Ba-Abbad et al. | 204/157.6 |

\* cited by examiner

*Primary Examiner* — Nina Bhat

(57) ABSTRACT

A method of treating sludge using solar energy is provided. The present invention utilizes a Fresnel panel frame that includes at least one Fresnel panel. The Fresnel panel may cover at least a portion of a bed cavity. An amount of waste may be placed within the bed cavity. When placed in sunlight, the heat enhanced by the Fresnel panels may heat the waste sufficiently for safe easy disposal, recycling, or for the creation of fertilizer.

12 Claims, 4 Drawing Sheets

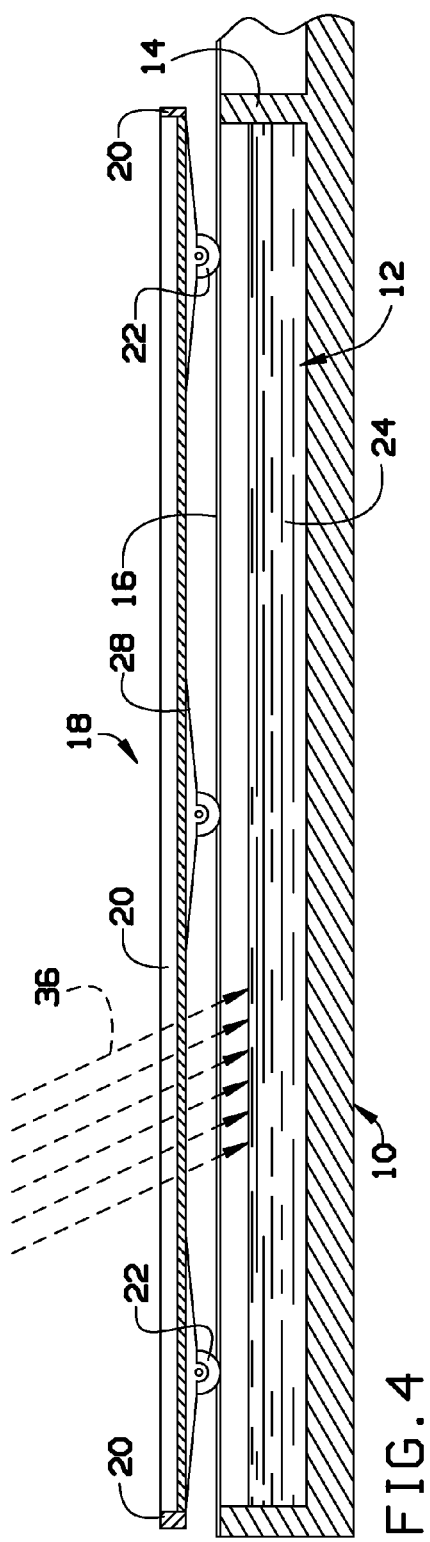
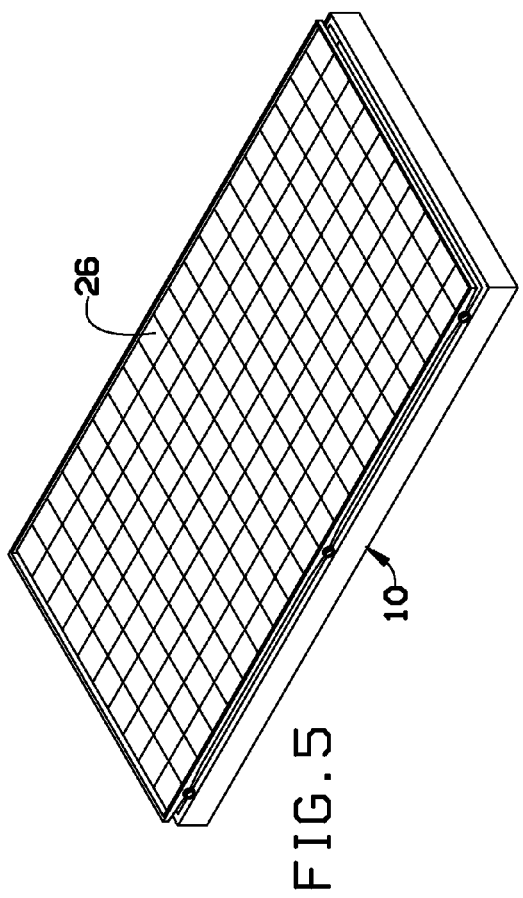

METHOD OF TREATING SLUDGE USING SOLAR ENERGY

CROSS-REFERENCE TO RELATED APPLICATION

This application is a continuation-in-part of application Ser. No. 13/745,266, filed Jan. 18, 2013.

BACKGROUND OF THE INVENTION

The present invention relates to a waste treatment device and, more particularly, to a waste treatment device that turns waste into disposable and usable products.

After the treatment of wastewater is performed, biosolids and the associated contaminants are removed. Biosolids are a solid, semisolid, or liquid residue. Biosolids that are used beneficially must be treated to reduce pathogens and vector attraction. Distribution and marketing of Class AA biosolid products is regulated by governments. Class AA biosolids are considered to be the highest quality of biosolids produced and may be utilized as fertilizer through commercial distribution and marketing.

Traditionally, biosolids (sludge) disposal involves trucking the sludge into rural areas and dumping the sludge onto fields. This may cause major health concerns. Other methods of disposal may include incineration, adding chemicals or dumping into landfills. However, concerns about contaminants, runoff, air pollution, tipping fees, and rising transportation costs have resulted in cities and municipalities seeking alternative and more efficient methods to handle the removal of wastewater biosolids.

Others have attempted various methods of biosolid pasteurization, but each method has shortcomings. For example, solar drying in greenhouses does not dry or heat sewage sludge and septic waste to a safe level. Gas drying or alkaline stabilization have high processing costs for energy, fuel and chemicals.

As can be seen, there is a need for efficient methods of treating wastes.

SUMMARY OF THE INVENTION

In one aspect of the present invention, a method of treating waste comprises: providing a treatment device comprising: a bed having a plurality of walls comprising a first sidewall, a second sidewall, a first end wall and a second end wall, wherein the plurality of walls create a bed cavity; and a Fresnel panel frame comprising at least one Fresnel panel; loading the waste into the bed cavity; covering at least a portion of the bed cavity with the Fresnel panel frame; heating the waste by providing a source of light to shine through the at least one Fresnel panel.

These and other features, aspects and advantages of the present invention will become better understood with reference to the following drawings, description and claims.

BRIEF DESCRIPTION OF THE DRAWINGS

FIG. 4 is a section detail view of the present invention along line 4-4 in FIG. 1;

FIG. 5 is a perspective view of an alternate embodiment of the present invention;

DETAILED DESCRIPTION OF THE INVENTION

Figure 1:
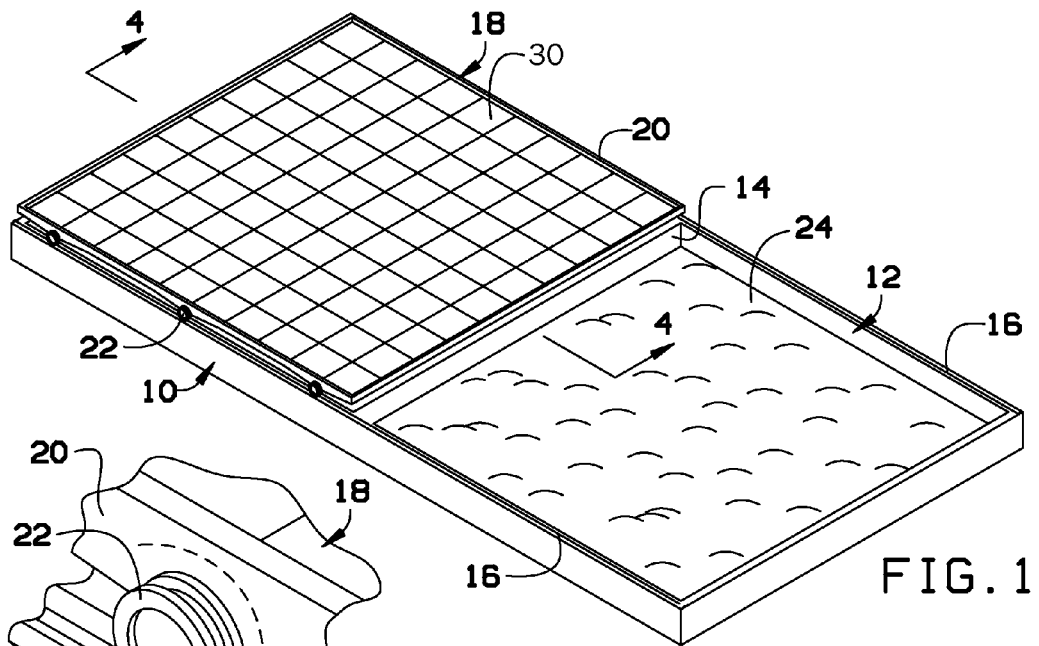
FIG. 1 is a perspective view of the present invention shown in use.
Figure 2:
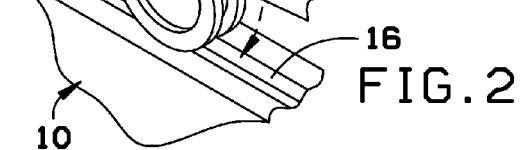
FIG. 2 is a detail perspective view of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a tank or bed having a plurality of sidewalls that create a bed cavity. A Fresnel panel frame that includes at least one Fresnel panel may be adjacent to the bed cavity and may cover at least a portion of the bed cavity. An amount of waste may be contained within the bed cavity. When placed in sunlight, the heat enhanced by the Fresnel panels may heat the waste sufficiently for easy disposal or for creating fertilizer.

Referring now to FIGS. 1 through 8, the present invention may include a tank or a bed 10. The tank or bed 10 may be made of any suitable materials, such as steel and/or concrete. The bed 10 may be enclosed by a plurality of walls. The plurality of walls may include a first end wall 38, a second end wall 40, a first sidewall 42, and a second sidewall 44. The plurality of walls may create a bed cavity 12. The bed cavity 12 may be configured to contain waste 24.

The waste 24 may be pumped or dumped into the bed cavity 12. The waste 24 may include, but is not limited to, wastewater, wastewater sludge (biosolids), septic waste, landfill leachate waste, septic sludge, grease trap waste, paper mill sludge, mining water, mining wastewater, and the like. In certain embodiments, the waste 24 may be pumped into the bed cavity 12 by a piping. However, the waste 24 may be shoveled or dumped into the bed cavity through a top opening.

Figure 3:
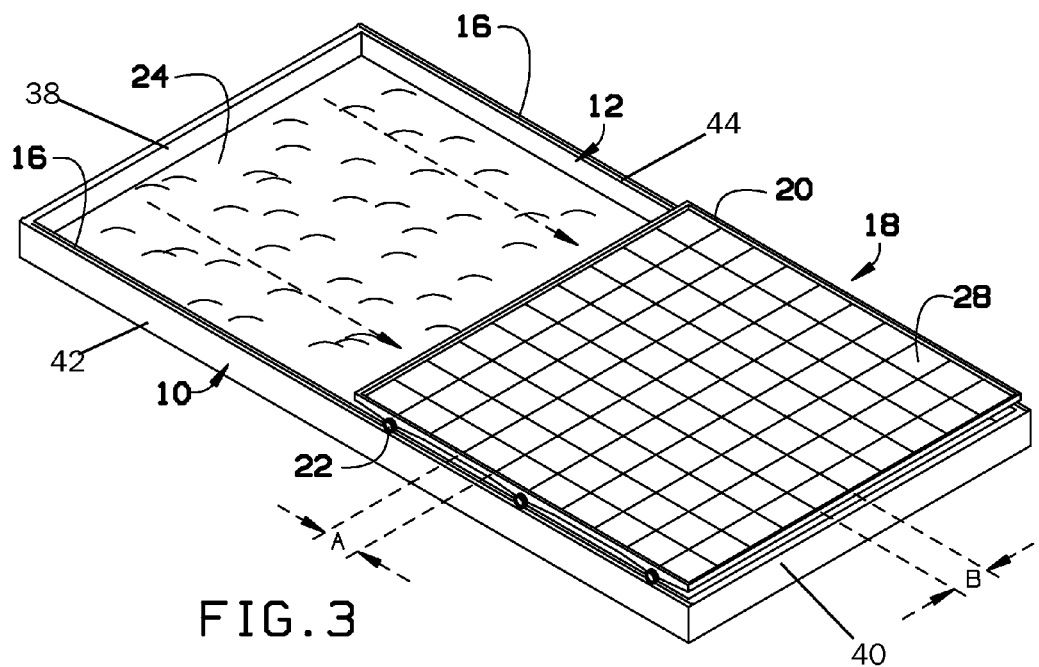
FIG. 3 is a perspective view of the present invention illustrated with the Fresnel sliding panel of FIG. 1 shown in a translated configuration.

In certain embodiments, the bed cavity 12 may include multiple compartments. The bed cavity 12 may include multiple compartments by way of a bed cavity divider 14. The bed cavity divider 14 may include walls that separate sections of the bed cavity 12. As illustrated in FIGS. 1, 3 and 4, the bed cavity divider 14 may divide the bed cavity 12 into two different sections or compartments. Multiple compartments within the bed cavity 12 may allow a user to include multiple stages of waste 24 treatment.

The present invention may include a Fresnel panel frame 20. The Fresnel panel frame 20 may include at least one Fresnel panel 30. In certain embodiments, the Fresnel panel frame 20 may include a plurality of Fresnel panels 30. The Fresnel panel frame 20 may be positioned adjacent to the plurality of sidewalls. In certain embodiments, the Fresnel panel frame 20 may rest or be attached to the top of the plurality of sidewalls. Thereby, the Fresnel panel frame 20 may at least partially cover the bed cavity 12. In certain embodiments, the Fresnel panel frame 20 may substantially cover the bed cavity 12 and in other embodiments, the Fresnel panel frame 20 may entirely cover the bed cavity 12.

The Fresnel panels 30 may be used to heat the waste 24 and thereby treat the waste 24. Heating the waste 24 provides for easy disposal or transforms the waste 24 into usable and safe fertilizer. Sunlight 36 may pass through the Fresnel panels 30 and sufficiently heat the waste 24. Any type of waste 24 may be heated to a high pasteurization temperature with rapid evaporation and pasteurization. The high temperatures facilitate the evaporation of moisture, and may include a rapid evaporation process, which may dry out all of the moisture and leave a granular or ash end product.

In certain embodiments, the Fresnel panels 30 may be used to heat the waste 24, such as sludge, for about 24 hours to about 72 hours to change the waste 24 into the usable fertilizer. However, in certain circumstances, the waste 24 may be treated for shorter or longer periods of time. For example, if there is a larger amount of waste 24 to be treated or the waste 24 contains more water than average, the waste 24 may take a longer amount of time stated.

Figures 6, 7:
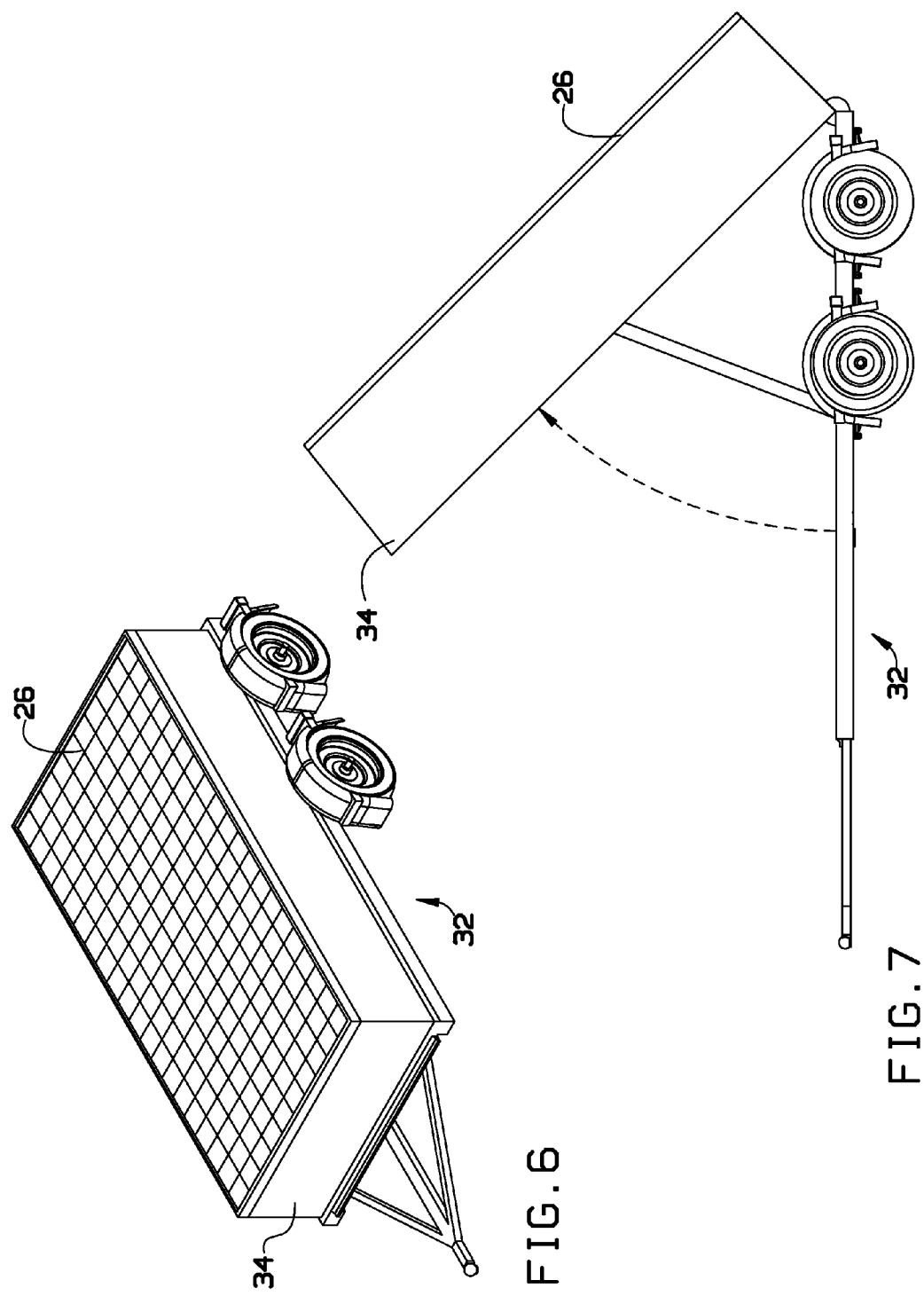
FIG. 6 is a perspective view of an alternate embodiment of the present invention.
FIG. 7 is a side view of the alternate embodiment of FIG. 6 shown with the trailer bed in a rotated configuration.

The Fresnel panels 30 may include a spot Fresnel panel 26, a linear Fresnel panel 28, or the like. As illustrated in FIG. 3, the Fresnel panel frame 20 may include the linear Fresnel panels 28. As illustrated in FIG. 6, the Fresnel panel frame 20 may include the spot Fresnel panels 26.

In certain embodiments, the present invention may include a Fresnel sliding panel assembly 18. The Fresnel sliding panel assembly 18 may enable a user to move the Fresnel panel frame 20 to different orientations to cover different areas of the bed cavity 12. In certain embodiments, the plurality of walls may include bed rails 16 in certain configurations of the Fresnel sliding panel assembly 18. As illustrated in FIGS. 1 and 3, the bed rails 16 may be located on top of the edge of the first side wall 42 and the second side wall 44. A roller wheel 22 may be attached to the Fresnel panel frame 20.

The roller wheel 22 may align with and be positioned on the bed rail 16. In such embodiments, the Fresnel panel frame 20 may be moved along the bed rail 16. Thereby, the Fresnel panel frame 20 may be in an orientation where the Fresnel panels 30 are closer to the first end 38 and the Fresnel panel frame 20 may be in an orientation where the Fresnel panels 30 are closer to the second end 40. The sliding panel assembly 18 may be automatic or manual. Therefore, a user may physically move the Fresnel panel frame 20 from one side to the other or an activated machine may move the Fresnel panel frame 20 from one side to the other. While in use, the Fresnel panel frame 20 may be moved from the first end 38 to the second end 40 after about 24 hours to about 72 hours.

In certain embodiments, the tank or bed 10 may include a material turner, mixer or rotary screw conveyor. The turner, mixer or rotary screw conveyor may include at least one rod aligned or screw conveyor at the bottom of the bed. The at least one rod may include ridges. The rod may also be powered or rotated manually. When the at least one rod is rotated, the waste 24 may turn and mix. This process may induce faster drying. It is envisioned that other turners and mixers may be used to serve the same purpose, and are thereby encompassed herein.

Once the waste 24, such as sludge, has been dried and processed into fertilizer, the fertilizer may be removed from the tank or bed 10 manually or by machine. For example, a removal machine may be attached directly to the bed 10 and may remove the fertilizer when activated. The fertilizer may be bagged and sold as Class AA organic fertilizer.

In certain embodiments, the present invention may be mounted on a trailer bed 34 or directly to a vehicle. This may allow for easy transportation of the processed waste 24. As illustrated in FIGS. 6 and 7, the present invention may include a trailer configuration 32. In such embodiments, once the waste 24 has been processed into fertilizer, the fertilizer may easily be dumped into the desirable location.

Figure 8:
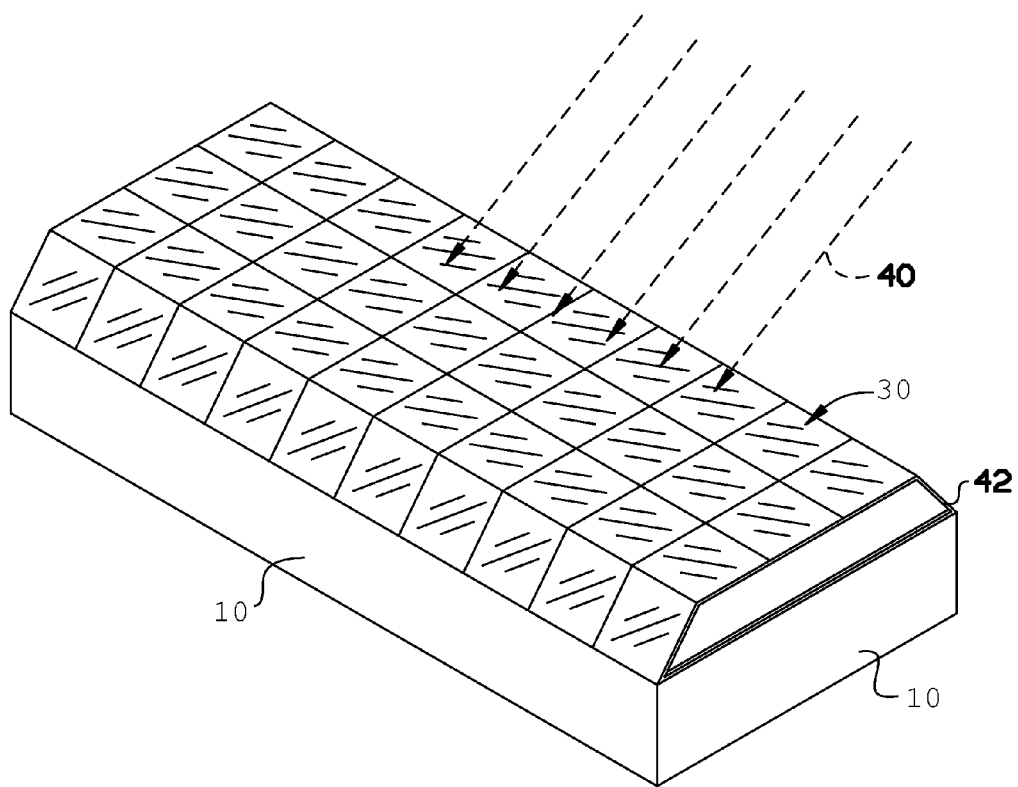
FIG. 8 is a perspective view of an alternate embodiment of the present invention.

FIG. 8 provides an alternative embodiment of the present invention. The Fresnel panel frame 20 with a plurality of Fresnel panels 30 may be fixed to the bed 10. The Fresnel panels 30 adjacent to the sidewalls may be oriented at an angle relative to the sidewalls, while Fresnel panels 30 on the top may be parallel with the bed 10. In such embodiments, there may be an opening 42 to load and unload the waste 24. Further, the bed 10 may include a tubular auto rotating chamber for a continuous flow processing. Once the waste 24 has been loaded, exemplary solar radiation 40 may heat up the waste 24 and thereby treat the waste.

A user may build or machine the treatment/processing tank or bed 10. In certain embodiments, the bed 10 sidewalls may be about 24 to about 60 inches tall. The bed cavity 12 may include a holding capacity of around 7,000 and up to around 100,000 gallons. The bed cavity size may be from about 30 cubic yard bed cavity up to about 500 cubic yards. However, the disclosure of such dimensions and holding capacities is for exemplary purposes only and it is envisioned that one skilled in the art may create the tank in any desired dimensions without departing from the scope of the present invention. In certain embodiments, the Fresnel panel frame 20 may cover half of the bed cavity 12. In certain embodiments, the tank or bed 10 may be exposed or may include a glass or polymer cover, such as Plexiglass®. In such embodiments, the half of that is not covered by the Fresnel Panels 20 may still be covered by the polymer cover.

A method of using the present invention may include the following. The waste 24 materials may be placed within the bed cavity 12. The Fresnel panel frame 20 with at least one Fresnel panel 30 may cover the bed cavity 12 at least partially. The sunlight may pass through the at least one Fresnel panel 30 and heat the waste 24. The Fresnel panel frame 20 may then slide from one side to the other to process two batches. The sludge may be dried and pasteurized. After full processing, the end product may then be removed. In alternative embodiments, the present invention may be placed in a standard greenhouse with a clear glass or polymer cover, such as Plexiglass® for weather protection prior to or during processing. This may keep rainwater from entering the Fresnel chambers and may also be used for storing the finished processed end products of the present invention during adverse weather conditions.

The following includes multiple treatment methods and end products for multiple waste products using the present invention. Water plant waste water and sludge may be treated to form a dry pasteurized granular, ash, or high grade fertilizer. Landfill Leachate liquid waste may be treated to evaporate all of the moisture, leaving only a residue or ash end product. Septic waste and septic sludge may be treated using the solar Fresnel heating process raising the temperature to pasteurization levels and causing rapid evaporation of the moisture. The end product may be a dry pasteurized granular, class AA fertilizer or ash. Grease trap waste may be treated through the solar Fresnel heating process raising the temperature to high temperature levels causing the grease and water to separate. The grease end product may be a product called brown grease that may be converted to biodiesel. The water that is separated may then be treated through the solar heating process raising the temperature to pasteurization levels and causing rapid evaporation of the moisture. The end product may be a dry granular or ash. Paper Mill sludge and waste may be treated using the solar Fresnel heating process raising the temperature to pasteurization levels and may evaporate all of the moisture at high pasteurization temperatures, creating a rapid evaporation process which may dry out all the moisture leaving a granular or an ash end product. Mining water may be processed through the Fresnel solar heating process raising the temperature to pasteurization levels causing rapid evaporation of the moisture, leaving a residue or ash end product.

It should be understood, of course, that the foregoing relates to exemplary embodiments of the invention and that modifications may be made without departing from the spirit and scope of the invention as set forth in the following claims.

What is claimed is:

1. A method of treating waste comprising:
    providing a treatment device comprising:
        a bed comprising at least one sidewall forming a bed cavity; and
        a Fresnel panel frame comprising at least one Fresnel panel;
    loading the waste into the bed cavity;
    covering at least a portion of the bed cavity with the Fresnel panel frame;
    heating the waste by providing a source of light to shine through the at least one Fresnel panel, wherein the at least one Fresnel panel enhances the heat of the light, converting the waste into fertilizer.

2. The method of claim 1, wherein the waste is at least one of wastewater, wastewater sludge (biosolids), septic waste, landfill leachate waste, septic sludge, grease trap waste, paper mill sludge, mining water, and mining wastewater.

3. The method of claim 1, wherein providing a source of light comprises light from the sun.

4. The method of claim 1, wherein the Fresnel panel frame comprises a plurality of Fresnel panels.

5. The method of claim 1, wherein the bed further comprises at least one bed cavity divider wall within the bed cavity creating at least two compartments within the bed cavity.

6. The method of claim 5, further comprising the step of alternating the covering between the at least two compartments of the bed cavity with the Fresnel panel frame in timed intervals.

7. The method of claim 6, wherein the Fresnel panel frame further comprises a Fresnel sliding panel assembly.

8. The method of claim 7, wherein the Fresnel sliding panel assembly comprises:
    a bed rail on the top edge of the first sidewall and the second sidewall; and
    a roller wheel attached to the Fresnel panel frame,
    wherein the roller wheel aligns with and rests within the bed rail.

9. The method of claim 1, wherein the at least one Fresnel panel is at least one spot Fresnel panel.

10. The method of claim 1, wherein the at least one Fresnel panel is at least one linear Fresnel panel.

11. The method of claim 1, wherein the bed further comprises a trailer bed supporting the bed of the apparatus.

12. The method of claim 1, wherein the bed further comprises in a rotating screw conveyor for continues flow processing of waste.

* * * * *